United States Patent [19]
Mathes

[11] 4,014,336
[45] * Mar. 29, 1977

[54] INHALATION DEVICE
[75] Inventor: Stanley Mathes, Mountain View, Calif.
[73] Assignee: Syntex Puerto Rico, Inc., Humacao, P.R.
[ * ] Notice: The portion of the term of this patent subsequent to Feb. 17, 1993, has been disclaimed.
[22] Filed: Nov. 20, 1975
[21] Appl. No.: 633,780

Related U.S. Application Data
[63] Continuation-in-part of Ser. No. 540,917, Jan. 13, 1975, Pat. No. 3,938,516.
[52] U.S. Cl. .............................. 128/266; 128/206; 128/208
[51] Int. Cl.$^2$ ................ A61M 13/00; A61M 15/06
[58] Field of Search .......... 128/205, 206, 208, 266; 222/193

[56] References Cited
UNITED STATES PATENTS

| | | | |
|---|---|---|---|
| 2,470,296 | 5/1949 | Fields | 128/206 |
| 2,470,296 | 5/1949 | Fields | 128/206 |
| 2,503,732 | 4/1950 | Heisterkamp | 128/207 |
| 2,517,482 | 8/1950 | Hall | 128/208 X |
| 2,587,215 | 2/1952 | Priestly | 128/206 |
| 2,672,865 | 3/1954 | Willis | 128/206 |
| 3,807,400 | 4/1974 | Cocozza | 128/266 |
| 3,858,583 | 1/1975 | Hallworth | 128/266 |

Primary Examiner—Aldrich F. Medbery
Attorney, Agent, or Firm—Joseph I. Hirsch; William B. Walker

[57] ABSTRACT

An inhalation device having an elongate housing having one or more passageways for the passage of air therethrough. Each passageway, of relatively small diameter, opens into an emptying chamber, of relatively greater diameter, adjacent that end of the housing which is adapted for insertion into the mouth or nose of a user. Adjacent that end of the emptying chamber closest to the passageway(s), the housing has means for receiving or presenting a unit dose of powdered medicament for administration. Means are provided to open the medicament holder as it is being inserted into, or after it has been inserted into, the means for receiving or presenting a unit dose of powdered medicament for administration. During inhalation, the air stream passing over and directed into the powdered medicament holder entrains the powdered medicament which is then carried into the nose, throat or lungs of the user where beneficial or therapeutic action of the medicament occurs.

28 Claims, 8 Drawing Figures

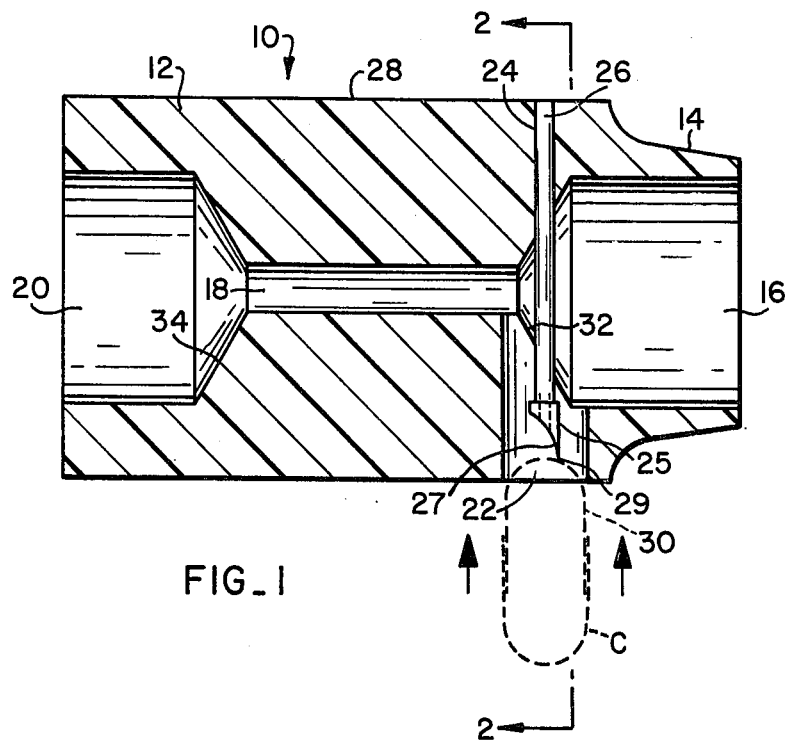
FIG_1
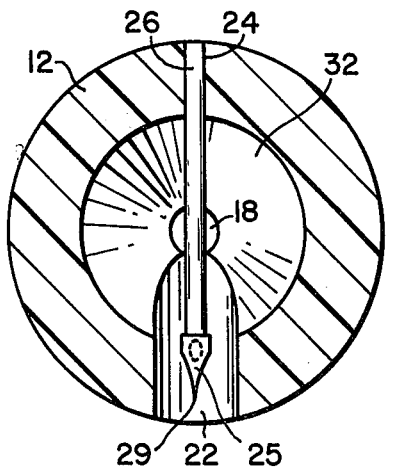
FIG_2
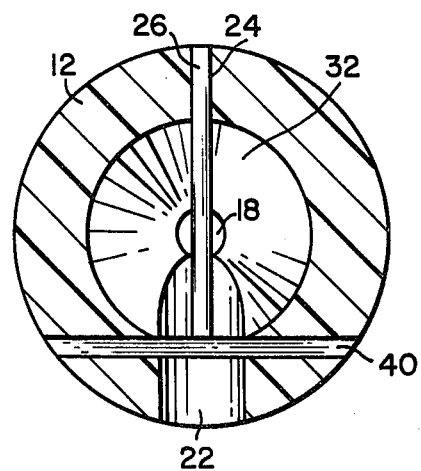
FIG_5

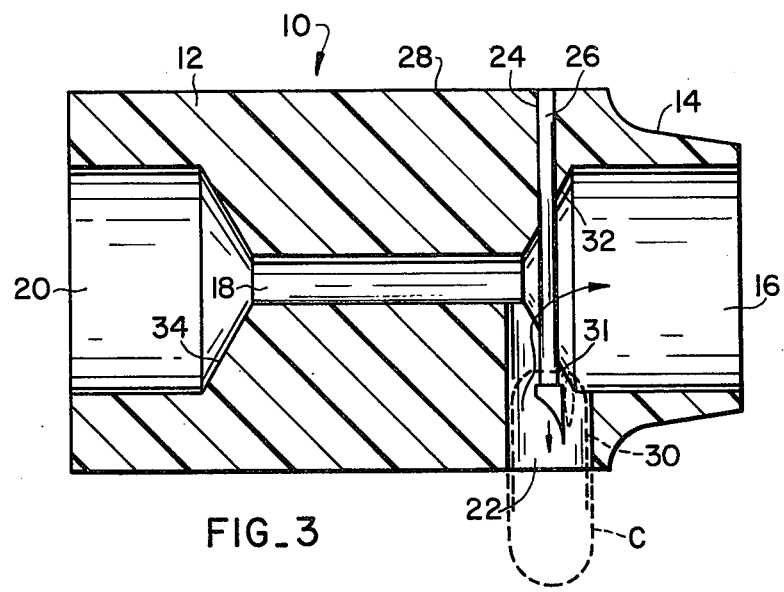
FIG_3
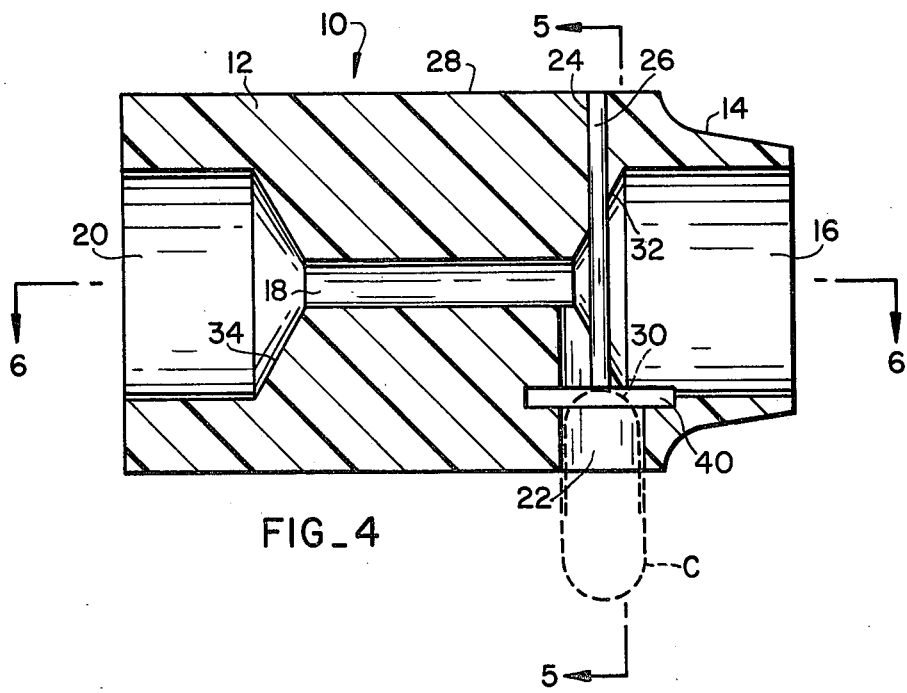
FIG_4

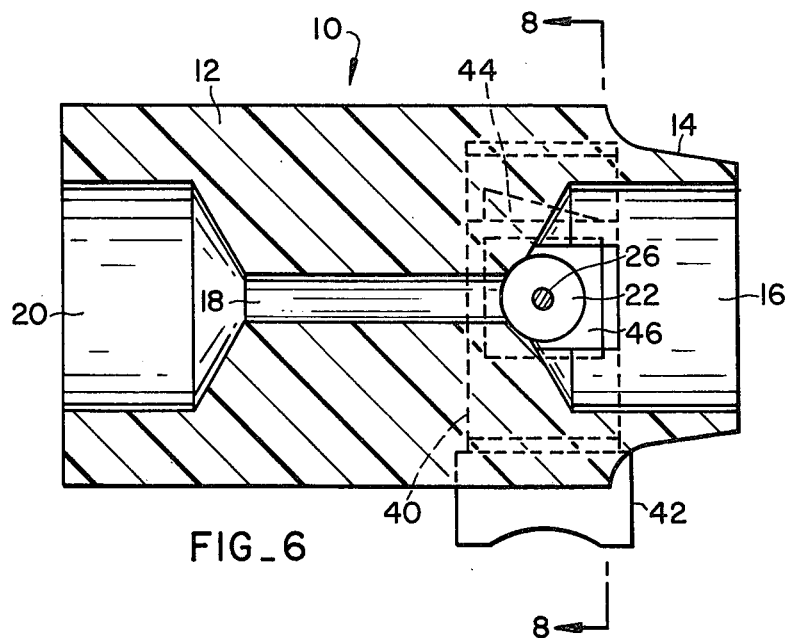
FIG_6
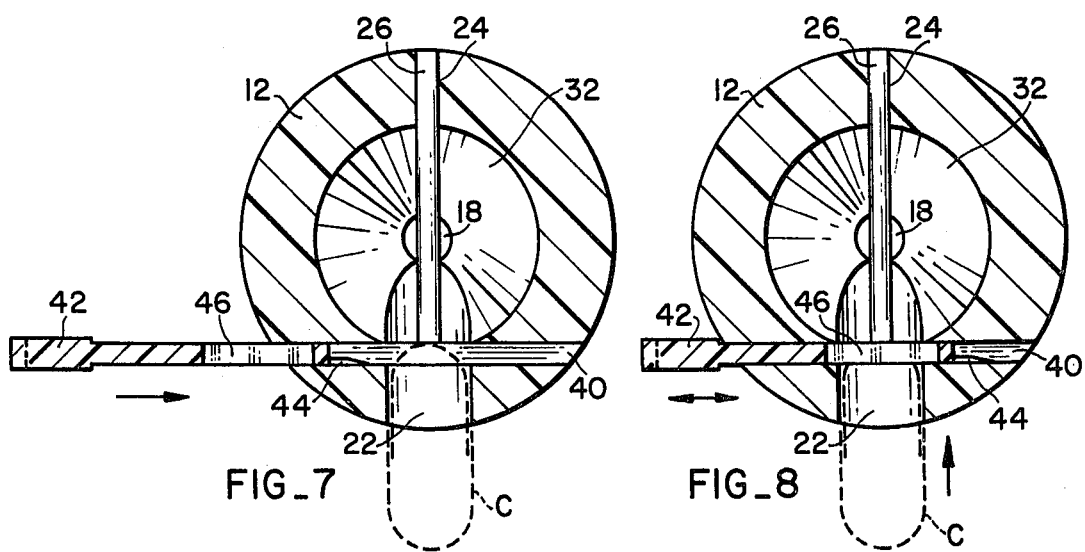
FIG_7  FIG_8

INHALATION DEVICE

REFERENCE TO PARENT APPLICATION

This application is a continuation-in-part of application Ser. No. 540,917, filed Jan. 13, 1975 and now U.S. Pat. No. 3,938,516.

FIELD OF THE INVENTION

This invention is related to devices for the administration of powdered medicaments by inhalation. More particularly, this invention relates to an inhalation device having, in the essential aspects thereof, no moving parts, yet which is capable of causing a powdered medicament, held within a container inserted into, or adjacent, the device, to be rapidly and effectively dispensed from the container, entrained in the air stream being inhaled and, thusly, carried into the nose, throat or lungs of the user where beneficial action of the medicament occurs.

BACKGROUND OF THE INVENTION

Known prior art inhalation devices include, for example, those shown in U.S. Pat. Nos. 988,352; 2,507,702; and 2,603,216; and Great Britain Patent No. 1,118,431.

SUMMARY OF THE INVENTION

The inhalation devices of the present invention include an elongate housing having one or more passageways for the passage of air therethrough, one end of the housing being adapted for insertion into the mouth or nose of a user. The passageway(s) extending through the housing terminate in an emptying chamber adjacent the output end of the housing. Means are provided adjacent the intersection of the passageway(s) with the emptying chamber for receiving or presenting a unit dose of powdered medicament for administration by inhalation. As shown, the housing has a port adapted to receive and hold a powdered medicament-holding container from which the medicament is to be entrained in the air stream passing through the device during inhalation. The container port can be slightly tilted (up to about 15° from the vertical) toward the passageway(s) (i.e., away from the output end of the housing) if desired, for example as shown in copending application Ser. No. 540,623, filed Jan. 13, 1975. The aforesaid device has means associated therewith for automatically opening the container as it is inserted into the device or means to open the container after it has been inserted into the device. In either case, such means eliminate the need to manually open the container prior to insertion, and, thusly, reduce the possibility of inadvertent spillage of the medicament prior to inhalation.

In one embodiment, an air stream tube disposed opposite the means for holding the container extends into the container and, during inhalation, directs a stream of air into the container which assists in causing the powdered medicament to be expelled from the container during the inhalation process. This embodiment is shown in FIGS. 1–3 described in greater detail below.

In a second embodiment, the device includes a slide having a sharp cutting edge which is manually pushed against the capsule, after it is inserted into the device, to slice open the top and thereby expose the medicament to be administered. This embodiment is shown in FIGS. 4–8 described in greater detail below.

Container, as used herein, is intended to include any means by which a unit dose of medicament is presented to the device for administration. Capsules are the presently preferred form of container; however, it is contemplated that other forms would be equally suitable if appropriate structural modifications of the device, to accommodate the different carrier, are made as, and if, necessary.

It has been found that, with the inhalation devices of this invention, the powdered medicament held within the container is rapidly and efficiently entrained in the air stream passing through the device during inhalation, and, as such, is carried into the nose, throat or lungs of the user where beneficial or therapeutic action of the medicament occurs.

BRIEF DESCRIPTION OF THE DRAWINGS

The foregoing and still further features and advantages of the present invention will become more apparent from the following detailed description, taken together with the accompanying drawings wherein:

FIG. 1 is a vertical cross-sectional view of one embodiment of an inhalation device of the present invention which has means for opening a medicament-holding container as it is being inserted into the device;

FIG. 2 is a cross-sectional view of the inhalation device of FIG. 1 taken along line 2—2 of FIG. 1;

FIG. 3 is a further cross-sectional view of the inhalation device of FIG. 1 showing the medicament-holding container after it has been opened by movement against the opening means;

FIG. 4 is a vertical cross-sectional view of an alternate embodiment of the inhalation device of the present invention which has means for opening a medicament-holding container after it has been inserted into the device;

FIG. 5 is a cross-sectional view of the inhalation device of FIG. 4 taken along line 5—5 of FIG. 4;

FIG. 6 is a longitudinal cross-sectional view of the inhalation device of FIG. 4 taken along line 6—6 of FIG. 4;

FIG. 7 is a cross-sectional view of the device of FIG. 4 taken along line 8—8 of FIG. 6 showing the opening means in the position before the medicament-holding container has been opened; and FIG. 8 is a cross-sectional view of the device of FIG. 4 taken along line 8—8 of FIG. 6 showing the opening means in the position after the medicament-holding container has been opened.

In the discussion below, reference will be made to a capsule as the exemplary container for presenting the medicament to the device for administration. As set forth above, other containers are contemplated for use with the devices of this invention.

Referring to FIG. 1, there is shown an inhalation device 10 having a substantially cylindrical elongate housing 12 (as can best be seen in FIG. 2). At one end of housing 12 is a mouthpiece 14 intended for insertion into the mouth of a user thereof. Mouthpiece 14 can be redesigned to provde a conventional shape to permit insertion into the nasal passages or, if desired, a conventional adapter (not shown) can be placed over the mouthpiece to permit nasal use. Adjacent mouthpiece 14 is an emptying chamber 16 connected at the inner end thereof to passageway 18 which, in turn, is connected, at the end thereof remote from emptying chamber 16, to incoming or entrance chamber 20. Chamber 20 is an optional element of device 10 and can be eliminated if desired, as shown, for example, in copending application Ser. No. 540,623, filed Jan. 13, 1975. Adjacent the lower, inner end of chamber 16, there is an opening or capsule holding port 22 into which an unopened capsule C, shown in dotted outline in FIG. 1, is inserted prior to inhalation. Directly opposite port 22 there is a cylindrical passageway 24 in which there is inserted a hollow air stream tube 26 which extends from adjacent the surface 28 of housing 12 into port 22 at a position below the upper surface of top 30 of opened capsule C (see FIG. 3). Optionally, the air stream tube can be integrally molded by well-known means into the device thereby eliminating the need for a separate tube 26. Tube 26 terminates in a lower portion 25 having a sharp edge 27 and a sharp point 29. As the capsule is inserted into port 22, the top thereof will come into contact with edge 27 and point 29 whereby, upon continued movement of the capsule, a hole (designated in FIG. 3 by flattened area 31) will be created in the capsule. During inhalation, air drawn through air stream tube 26 is directed into the opened capsule and assists in causing the medicament to be expelled from the capsule through the annular space between the exterior surface of the tube and the adjacent edge of the hole cut in the top of the capsule by the lower edge of the tube, which, as shown in FIG. 3, is sufficiently below the top of the capsule to permit expulsion of the powdered medicament through the annular space. Slanted surfaces 32 and 34 connect cylindrical chambers 16 and 20 with cylindrical passageway 18, respectively, as can best be seen in FIGS. 1 and 3. The manner of connecting passageway 18 with chambers 16 and 20 can be more squared-off or streamlined, as desired, as long as the particular configuration selected is effective to cause the powdered medicament to be expelled from the capsule, in the desired number of inhalations, during the inhalation, medicament-administering process.

In use, the patient manually inserts the unopened medicament-holding capsule, or other medicament-holding container, into port 22. As the capsule is moved from the position shown in FIG. 1 to the position shown in FIG. 3, the top 30 thereof comes into contact with lower edge 27 of tube 26, which then cuts a hole in the top of the capsule as it is fully inserted into the device. The mouthpiece is then taken into the mouth and, upon inhalation, the air flowing through the device causes the medicament in the capsule to be entrained in the air stream flowing through emptying chamber 16. In this manner, the medicament is carried through the mouth and into the throat or lungs of the user where beneficial or therapeutic action of the medicament occurs.

A further embodiment of the inhalation devices of the present invention is shown in FIGS. 4–8 where like numerals as used in FIGS. 1–3 are utilized to represent like elements. Referring to FIGS. 4–8, the inhalation device shown therein has a channel 40 extending transversely to the longitudinal axis of the device. Slide 42 moveable within channel 40 has a sharp blade 44 fixedly secured to the leading edge thereof. After partial insertion of unopened capsule C into port 22, the slide is moved laterally to slice open the top of the capsule and thereby expose the medicament to be administered, the severed part of the capsule being preferably ejected out of the device through the far end of channel 40. The capsule can be left as shown in FIG. 8 during inhalation, or, preferably, pushed further up in port 22 through opening 46 in slide 42, or slide 42 can be withdrawn, with or without further upward movement of the capsule. In this manner, the capsule is opened after insertion into the device and the contents thereof exposed for administration.

The opening means described above and other means equivalent thereto, which eliminate the need to manually open the container prior to insertion thereof into the inhalation device, are considered to be within the scope of this invention.

The entire device can be made of metal but preferably is made of suitable plastic material, such as nylon, polyacetal and polypropylene. The air stream tube can either be plastic, such as those referred to above, or a metal tube, such as, for example, a surgical needle, etc. With the exception of the capsule or other medicament-holding container, the device, in its basic elements, is preferably of unitary construction, although multi-piece construction is contemplated, especially where means are provided to open the medicament-holding container.

The physical properties (i.e., flow characteristics) of each medicament formulation will affect the ease or manner in which it is dispensed with these or other inhalation devices. However, for a given powdered formulation, varying the diameter of passageway 18, the positioning of port 22 (from the position as shown toward the open end of chamber 16), the diameter of tube 26 or the distance it extends above or below the longitudinal axis of passageway 18 or the device, the tilt of the container opening or port at an angle to about 15° from the vertical toward passageway 18 and the depth to which the container is inserted into the opening, and/or, in general, the overall configuration and shape of chambers 16 and 20 and the passageway(s), devices can be designed to deliver the medicament in a different number of inhalations or in a longer or shorten period of time, depending upon the nasal or lung capacities of each particular user. Quite obviously, no single device will be suitable for all persons requiring administration of powdered medicaments since, for example, people with differing lung capacities are known to generate flow rates from about 30 liters/minute or so to about 120 liters/minute or so through inhalation devices of this and known types. Nonetheless, the devices of this invention afford such variability, through proper selection of the various design parameters, that a device, embraced within the scope of this invention, can be designed for a particular patient-generated flow rate to deliver the medicament according to a certain set of pre-determined objections (e.g., slow or fast administration, one or more inhalations, etc.). The net result is that a family of devices, all embraced within the present invention, can be designed, each of which will deliver the medicament under a given set of selected administration conditions. Conversely, the devices of this invention can be designed to cover an extensive range of operating conditions, and thus be made suitable for use by a variety of persons having differing inhalation abilities or capacities.

While the present invention has been described with reference to specific embodiments thereof, it will be understood by those skilled in the art that various changes may be made and equivalents may be substituted without departing from the true spirit and scope of the invention. For example, as set forth above, the actual shape of the chambers 20 and 16 can be modified, as by streamlining, or, if desired, chamber 20 can be eliminated in toto; passageway 18 (and chamber 20) can be eliminated in toto; more than one passageway can be provided; the longitudinal passageway or passageways can be replaced by radially extending passageway; etc. Additionally, other modifications may be made to adapt a particular situation, material or composition of matter, structural desirability, or then-present objective to the spirit of this invention without departing from its essential teachings.

What is claimed is:

1. An inhalation device comprising an elongate housing having a passageway for the movement of air therethrough, one end of said housing being an output end adapted for insertion into the mouth or nasal passages of a user thereof; said passageway terminating in an emptying chamber adjacent the output end of said housing, the cross-sectional area of said passageway being less than the cross-sectional area of said emptying chamber; means for receiving a closed medicament-holding container; means to open the medicament-holding container as the container is inserted into said container receiving means; and hollow means for directing a stream of air drawn therethrough during inhalation into an opened medicament-holding container positioned within said container receiving means, whereby air drawn through said passageway and through said hollow means cooperate to cause the medicament in the medicament-holding container to be dispensed therefrom.

2. The device of claim 1 wherein said container receiving means comprises a first opening in said housing adjacent said emptying chamber.

3. The device of claim 2 wherein said first opening is tilted toward said passageway at an angle up to about 15° from the vertical.

4. The device of claim 1 wherein the axis of said passageway lies along the longitudinal axis of said housing.

5. The device of claim 1 wherein said hollow means comprises a second opening in said housing and a hollow tube disposed therein, and said container opening means comprises a sharp enlarged point on the tip of said hollow tube closest to said container receiving means, said sharp point serving to open a closed medicament-holding container as the container is inserted into said container receiving means, said tip of said hollow tube extending into the opened medicament-holding container held by said container receiving means during inhalation to a point above the level of the medicament therein but below the top of the container whereby, during inhalation, the medicament is dispensed from the container through the space defined by the outer surface of said hollow tube and the inner surface of the opening in the top of the container.

6. The device of claim 1 wherein said hollow means comprises a hollow tube-like passageway in said housing, said hollow tube-like passageway having a sharp, enlarged end portion at the end thereof closest to said container receiving means, said sharp end serving to open a closed medicamentholding container as the container is inserted into said container receiving means, said enlarged end of said hollow tube-like passageway extending into the opened medicament-holding container held by said container receiving means during inhalation to a point above the level of the medicament therein but below the top of the container whereby, during inhalation, the medicament is dispensed from the container through the space defined by the outer surface of said hollow tube-like passageway and the inner surface of the opening in the top of the container.

7. The device of claim 1 wherein said emptying chamber and said passageway are substantially cylindrical.

8. The device of claim 1 wherein said container receiving means is closely adjacent the interface between said passageway and said emptying chamber.

9. An inhalation device comprising an elongate housing having a passageway for the movement of air therethrough, one end of said housing being an output end adapted for insertion into the mouth or nasal passages of a user thereof; said passageway terminating in an emptying chamber adjacent the output end of said housing, the cross-sectional area of said passageway being less than the cross-sectional area of said emptying chamber; means for receiving a closed medicament-holding container; means to open the medicament-holding container after the container is inserted into said container receiving means; and hollow means for directing a stream of air drawn therethrough during inhalation into an opened medicament-holding container positioned within said container receiving means, whereby air drawn through said passageway and through said hollow means cooperate to cause the medicament in the medicament-holding container to be dispensed therefrom.

10. The device of claim 9 wherein said container receiving means comprises a first opening in said housing adjacent said emptying chamber.

11. The device of claim 10 wherein said first opening is tilted toward said passageway at an angle up to about 15° from the vertical.

12. The device of claim 9 wherein the axis of said passageway lies along the longitudinal axis of said housing.

13. The device of claim 9 wherein said emptying chamber and said passageway are substantially cylinderical.

14. The device of claim 9 wherein said container receiving means is closely adjacent the interface between said passageway and said emptying chamber.

15. The device of claim 9 wherein said container opening means comprises a channel extending substantially transversely to said passageway through said housing at a point adjacent said container receiving means, and a slide moveable in said channel, said slide having a sharp leading edge whereby, when said slide is pushed against the top of a medicament-holding container held within the container receiving means, the top of the container is sliced open to thereby expose the medicament therein.

16. The device of claim 15 wherein said slide further includes an opening therein adapted to be positioned between said hollow means and the opened medicament-holding container when said slide has been moved to the position where the top of the medicament-holding container has been opened to expose the medicament therein.

17. An inhalation device comprising an elongate housing having a passageway for the movement of air therethrough, one end of said housing being an output end adapted for insertion into the mouth or nasal passages of a user thereof; said passageway connecting an entrance chamber and an emptying chamber adjacent the output end of said housing, the cross-sectional area of said passageway being less than the cross-sectional area of either said entrance chamber or said emptying chamber; a first opening in said housing adjacent the interface between said passageway and said emptying chamber for receiving a closed medicament-holding container; means to open the medicament holding container as the container is inserted into said container receiving means; a second opening in said housing disposed opposite said first opening; said hollow means positioned within said second opening for directing a stream of air drawn therethrough during inhalation into an opened medicament-holding container positioned within said first opening, whereby, during inhalation, air drawn through said passageway and through said hollow means cooperate to cause the medicament in the container to be dispensed therefrom.

18. The device of claim 17 wherein said hollow means comprises a hollow tube disposed in said second opening, and said container opening means comprises a sharp enlarged point on the tip of said hollow tube closest to said first opening, said sharp point serving to open a closed medicamentholding container as the container is inserted into said container receiving means, said tip of said hollow tube extending into the opened medicament-holding container held within said first opening during inhalation to a point above the level of the medicament therein but below the top of the container whereby, during inhalation, the medicament is dispensed from the container through the space defined by the outer surface of said hollow tube and the inner surface of the opening in the top of the container.

19. The device of claim 17 wherein said hollow means comprises a hollow tube-like passageway in said housing, said hollow tube-like passageway having a sharp, enlarged end portion at the end thereof closest to said first opening, said sharp end serving to open a closed medicament-holding container as the container is inserted into said container receiving means, said enlarged end of said hollow tube-like passageway extending into the opened medicament-holding container held within said first opening during inhalation to a point above the level of the medicament therein but below the top of the container whereby, during inhalation, the medicament is dispensed from the container through the space defined by the outer surface of said hollow tube-like passageway and the inner surface of the opening in the top of the container.

20. An inhalation device comprising an elongate housing having a passageway for the movement of air therethrough, one end of said housing being an output end adapted for insertion into the mouth or nasal passages of a user thereof; said passageway connecting an entrance chamber and an emptying chamber adjacent the output end of said housing, the cross-sectional area of said passageway being less than the cross-sectional area of either said entrance chamber or said emptying chamber; a first opening in said housing adjacent the interface between said passageway and said emptying chamber for receiving a closed medicament-holding container; means to open the medicament holding container after the container is inserted into said container receiving means; a second opening in said housing disposed opposite said first opening; and hollow means positioned within said second opening for directing a stream of air drawn therethrough during inhalation into an opened medicament-holding container positioned within said first opening, whereby, during inhalation, air drawn through said passageway and through said hollow means cooperate to cause the medicament in the container to be dispensed therefrom.

21. The device of claim 20 wherein said container opening means comprises a channel extending substantially transversely to said passageway through said housing at a point adjacent said first opening, and a slide moveable in said channel, said slide having a sharp leading edge whereby, when said slide is pushed against the top of a medicamentholding container held within said first opening, the top of the container is sliced open to thereby expose the medicament therein.

22. The device of claim 21 wherein said slide further includes an opening therein adapted to be positioned between said hollow means and the opened medicament-holding container when said slide has been moved to the position where the top of the medicament-holding container has been opened to expose the medicament therein.

23. An inhalation device consisting essentially of a housing having an output end adapted for insertion into the mouth or nasal passages of a user thereof; said housing having a hollow emptying chamber adjacent the output end thereof; means adjacent said emptying chamber for receiving and holding a closed medicamentholding container without movement during inhalation; means to open the medicament-holding container as the container is inserted into said container receiving means; and hollow means for directing a concentrated stream of air drawn therethrough during inhalation directly into an opened medicament-holding container held within said container receiving means, whereby air drawn through said hollow means during inhalation flows directly into the medicament-holding container whereby the medicament therein is dispensed therefrom.

24. The device of claim 23 wherein said container receiving means comprises an exterior opening in said housing for receiving a closed medicament-holding container directly from the exterior of said device.

25. The device of claim 23 wherein said container opening means comprises a sharp enlarged point on the end of said hollow means closest to said container receiving means, said sharp point serving to open a closed medicamentholding container as the container is inserted into said container receiving means, said end of said hollow means extending into the opened medicament-holding container held by said container receiving means during inhalation to a point above the level of the medicament therein but below the top of the container whereby, during inhalation, the medicament is dispensed from the container through the space defined by the outer surface of said hollow means and the inner surface of the opening in the top of the container.

26. An inhalation device consisting essentially of a housing having an output end adapted for insertion into the mouth or nasal passage of a user thereof; said housing having a hollow emptying chamber adjacent the output end thereof; means adjacent said emptying chamber for receiving and holding a closed medicamentholding container without movement during inhalation; means to open the medicament-holding container after the container is inserted into said container receiving means; and hollow means for directing a concentrated stream of air drawn therethrough during inhalation directly into an opened medicament-holding container held within said container receiving means, whereby air drawn through said hollow means during inhalation flows directly into the medicament-holding container whereby the medicament therein is dispensed therefrom.

27. The device of claim 26 wherein said container receiving means comprises an exterior opening in said housing for receiving a closed medicament-holding container directly from the exterior of said device.

28. The device of claim 26 wherein said container opening means comprises a channel extending substantially transversely to said passageway through said housing at a point adjacent said container receiving means, and a slide moveable in said channel, said slide having a sharp leading edge whereby, when said slide is pushed against the top of a medicament-holding container held within the container receiving means, the top of the container is sliced open to thereby expose the medicament therein.

* * * * *